United States Patent [19]

Blum et al.

[11] 4,407,761

[45] Oct. 4, 1983

[54] PROCESS FOR THE PRODUCTION OF ω-AMINO-1-HYDROXYALKYLIDENE-1,1-BISPHOSPHONIC ACID

[75] Inventors: Helmut Blum; Karl-Heinz Worms, both of Dusseldorf, Fed. Rep. of Germany

[73] Assignee: Henkel Kommanditgesellschaft auf Aktien, Dusseldorf-Holthausen, Fed. Rep. of Germany

[21] Appl. No.: 254,918

[22] Filed: Apr. 16, 1981

[30] Foreign Application Priority Data

Apr. 28, 1980 [DE]  Fed. Rep. of Germany ....... 3016289

[51] Int. Cl.³ ................................................. C07F 9/38
[52] U.S. Cl. .............................. 260/502.5 C; 252/180
[58] Field of Search ....................................... 260/502.5

[56] References Cited

U.S. PATENT DOCUMENTS

| | | | |
|---|---|---|---|
| 4,054,598 | 10/1977 | Blum et al. ...................... | 260/502.5 |
| 4,267,108 | 5/1981 | Blum et al. ..................... | 260/502.5 C |
| 4,267,108 | 5/1981 | Blum et al. ...................... | 260/502.5 |
| 4,304,734 | 12/1981 | Jary et al. ....................... | 260/502.5 |
| 4,327,039 | 4/1982 | Blum et al. ..................... | 260/502.5 C |

FOREIGN PATENT DOCUMENTS

| | | |
|---|---|---|
| 2130794 | 1/1973 | Fed. Rep. of Germany . |
| 2658961 | 6/1973 | Fed. Rep. of Germany . |
| 2702631 | 7/1978 | Fed. Rep. of Germany . |
| 2745083 | 4/1979 | Fed. Rep. of Germany ... 260/502.5 |

OTHER PUBLICATIONS

Bulletin of Academy of Sciences of the USSR vol. 27, No. 2, Pt. 2 (1978.02).
M. I. Kabachnik et al. "Synthesis and Acid–Base and Complexing Properties of Amino–Substituted α-Hydroxyalkylidenediphosphonic Acids" pp. 374–377.

*Primary Examiner*—J. E. Evans
*Attorney, Agent, or Firm*—Hammond & Littell, Weissenberger and Muserlian

[57] ABSTRACT

A process for the preparation of a ω-amino-1-hydroxyalkylidine-1,1-biphosphonic acid of the formula

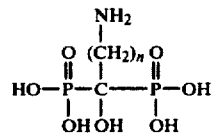

wherein n is an integer from 3 to 5, consisting essentially of the steps of reacting an aminocarboxylic acid of the formula $$NH_2-CH_2-(CH_2)_m-COOH$$

wherein m is an integer from 2 to 4, with a phosphonating reactant selected from the group consisting of
(a) a mixture of phosphorous acid and $PCl_3$,
(b) a mixture of phosphorous acid and $PCl_5$, and
(c) a mixture of phosphorous acid and $POCl_3$, hydrolyzing the reaction mixture with a strong acid which does not oxidize aminophosphonic acids, and recovering said ω-amino-1-hydroxyalkylidene-1,1-bisphosphonic acid.

4 Claims, No Drawings

PROCESS FOR THE PRODUCTION OF ω-AMINO-1-HYDROXYALKYLIDENE-1,1-BIS-PHOSPHONIC ACID

BACKGROUND OF THE INVENTION

This invention relates to an improved process for the preparation of ω-amino-1-hydroxyalkylidene-1,1-bisphosphonic acids of the formula (1) indicated below, where the end products are obtained in a particularly pure form.

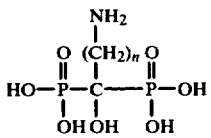

(n = 3 to 5)

It is known according to DE AS 21 30 794 to prepare 3-amino-hydroxypropylidene-1,1-bisphosphonic acid by the reaction of β-alanine with phosphorous acid and phosphorous trichloride and subsequent hydrolysis by the addition of water. But when this procedure is used in the reaction of 4-aminobutyric acid with $H_3PO_3/PCl_3$ and subsequent hydrolysis after the addition of water, a phosphonic acid mixture is obtained, as it can be determined by chromatographic tests.

This phosphonic acid mixture is substantially stable even if the solution is boiled for several hours. When boiling with 30% sodium hydroxide solution, the phosphonic acid mixture is likewise stable.

In practice, phosphonic acids according to Formula I could, therefore, not be obtained in pure form according to the known procedure without great expenditures.

Similar is the situation in the phosphonylation of 6-aminohexanoic acid. Here, too, a reaction mixture is obtained after hydrolysis which contains several different phosphonic acids.

Other processes for the production of 3-aminohydroxypropylidene-1,1-bisphosphonic acid by reaction of a β-alanine with a phosphonating agent under various conditions and subsequent hydrolysis with water, have been reported in DE-AS No. 2,658,961, DE-OS No. 2702631 and our copending U.S. patent application Ser. No. 192,733, filed Oct. 1, 1980, now U.S. Pat. No. 327,039.

OBJECTS OF THE INVENTION

An object of the present invention is the development of a process for the production of ω-amino-1-hydroxyalkylidene-1,1-bisphosphonic acid in good yields without complicated hydrolysis and recovery steps.

Another object of the present invention is the development of a process for the preparation of a ω-amino-1hydroxyalkylidine-1,1-bisphosphonic acid of the formula

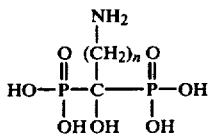

wherein n is an integer from 3 to 5, consisting essentially of the steps of reacting an aminocarboxylic acid of the formula $$NH_2-CH_2-(CH_2)_m-COOH$$

wherein m is an integer from 2 to 4, with a phosphonating reactant selected from the group consisting of
(a) a mixture of phosphorous acid and $PCl_3$,
(b) a mixture of phosphorous acid and $PCl_5$, and
(c) a mixture of phosphorous acid and $POCl_3$, hydrolyzing the reaction mixture with a strong acid which does not oxidize aminophosphonic acids, and recovering said ω-amino-1-hydroxyalkylidene-1,1-bisphosphonic acid.

These and other objects of the invention will become more apparent as the description thereof proceeds.

DESCRIPTION OF THE INVENTION

It has now been found that pure X-ray crystalline ω-amino-1-hydroxyalkylidene-1,1-bisphosphonic acid products can surprisingly be obtained when using the procedure of the invention.

The subject matter of the invention is, therefore, the preparation of compounds of Formula I, where n denotes an integer from 3 to 5, by the reaction of an ω-amino-alkane-carboxylic acid with phosphonylating agents and subsequent hydrolysis, which is characterized in that aminocarboxylic acids of the general formula $$H_2N-CH_2-(CH_2)_m-COOH \qquad (II)$$

where m denotes an integer from 2 to 4, are reacted with a mixture of phosphorous acid and $PCl_3$ or $PCl_5$ or phosphorous acid and $POCl_3$, and the reaction mixture is hydrolyzed with a strong acid which does not oxidize the aminophosphonic acid.

More particularly, the present invention relates to a process for the preparation of a ω-amino-1-hydroxyalkylidine-1,1-bisphosphonic acid of the formula

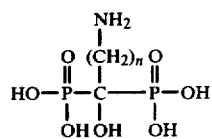

wherein n is an integer from 3 to 5, consisting essentially of the steps of reacting an aminocarboxylic acid of the formula $$NH_2-CH_2-(CH_2)_m-COOH$$

wherein m is an integer from 2 to 4, with a phosphonating reactant selected from the group consisting of
(a) a mixture of phosphorous acid and $PCl_3$,
(b) a mixture of phosphorous acid and $PCl_5$, and
(c) a mixture of phosphorous acid and $POCl_3$, hydrolyzing the reaction mixture with a strong acid which does not oxidize aminophosphonic acids, and recovering said ω-amino-1-hydroxyalkylidene-1,1-bisphosphonic acid.

The aminoalkane carboxylic acids of Formula II which can be used are 4-aminobutyric acid, 5-aminovaleric acid and 6-aminocaproic acid. The phosphonylation reaction generally takes place at temperatures of from 80° to 130° C., preferably at about 100° C.

Preferably 1 to 2, particularly 1.5 moles of $H_3PO_3$ and 1 to 2, particularly 1.5 mols of $PCl_3$ and/or $PCl_5$, or POCl₃ are used per mol of aminocarboxylic acid. If desired, PCl₅ can also be replaced by mixture of PCl₃ and chlorine. If the process is carried in the last described manner, it is of advantage if a mixture of aminocarboxylic acid, H₃PO₃ and PCl₃ in a molar ratio of 1:1:1 is prepared first and a corresponding amount of chlorine is introduced later.

If desired, inert organic diluents, which do not solubilize the reaction product, particularly chlorinated hydrocarbons, such as chlorobenzene, tetrachloroethane, tetrachloroethylene, and trichloroethylene, and dioxane can be used in the reaction. Particularly, however, when using phosphorous acid and POCl₃ as the phosphonating agent, it is not necessary to use a diluent. But if a diluent is used, it is removed after the reaction is completed. The remaining reaction product is then hydrolyzed with strong acids which do not act as oxidants for the aminophosphonic acids.

Strong acids which do not act as oxidants for aminophosphonic acids, are, for example, p-toluenesulfonic acid, hydrochloric acid, hydrobromic acid, trichloroacetic acid or those of comparable acid strength. Preferably concentrated hydrochloric acid is employed. The strong acids are preferably employed in aqueous solution.

In general, the hydrolysis is completed after about 3 hours boiling under reflux, as is shown by the chromatographic test of the reaction solution.

The aminoalkane diphosphonic acids described here are characterized by a sequestering power for polyvalent metal ions, particularly alkaline earth ions, as well as heavy metal ions, like iron and copper. They can also be used specifically for water softening. When so employed, it is not necessary to work with stoichiometric quantities, calcite precipitations can also be considerably delayed by substoichiometric quantities.

Because of their properties, they are also suitable for the production of cosmetic and pharmaceutical preparations.

The following examples are illustrative of the practice of the invention without being limitative in any manner.

EXAMPLE 1

0.5 mol of 4-aminobutyric acid and 0.75 mol of phosphorous acid were heated in 250 ml of chlorobenzene to 100° C. Then 0.75 mol of phosphorus trichloride were added dropwise at this temperature under vigorous stirring. After ending the dropwise addition, the heating was continued for 3 hours whereby a yellow-orange colored solid reaction was formed.

After cooling, the diluent, chlorobenzene, was decanted from the solid reaction product. As the continuous chromatographic control showed, the reaction product contained, in addition to monophosphoric and phosphorous acid, 3 to 4 different phosphonic acids.

This solid residue was then boiled to 300 ml of concentrated hydrochloric acid. After boiling for 3 hours under reflux, the total hydrolysis to a homogenous product could be determined by paper chromatography. By adding about 3 liters of acetone to the hydrolysate, the 4-amino-1-hydroxybutylidene-1,1-bisphosphonic acid was obtained in crystalline form. In order to free the substance of adhering phosphorous acid, it was boiled in some water, filtered through a frit, and dried in the vacuum-drying cabinet.

Yield: 69.7 gm = 56.0%. Analysis: Mol mass according to pH-titration: 250.4; calculated: 249. Paper chromatogram: pure compound Melting Point: 229° C.

| Elementary Analysis: | | | | |
|---|---|---|---|---|
| % | P | C | N | H |
| found | 25.1 | 19.7 | 5.92 | 5.21 |
| calc. | 24.90 | 19.28 | 5.62 | 5.22 |

EXAMPLE 2

0.5 mol of 4-aminobutyric acid were added under stirring to a mixture of 1 mol of phosphorous acid and 1 mol of phosphoryl chloride. After stirring for another 10 minutes at room temperature, the mixture was heated slowly to 100° C. A white foamy reaction product that could no longer be stirred was formed at 70° to 80° C., which was heated for another 3 hours to 100° C. The further treatment, separation of the diluent and treatment with conc. hydrochloric acid, was the same as in Example 1.

Yield: 56.1 gm = 45.1% Analysis Mol Mass according to pH-titration: 248.5; cal. 249 Paper chromatogram: pure compound Melting Point: 228° C.

| Elementary Analysis: | | | | |
|---|---|---|---|---|
| % | P | C | N | H |
| found | 24.8 | 19.3 | 5.77 | 5.47 |
| calc. | 24.90 | 19.28 | 5.62 | 5.22 |

EXAMPLE 3

0.5 mol of 6-aminocaproic acid was reacted with 0.75 mol of phosphorous acid and 0.75 mol of phosphorus trichloride under the conditions indicated in Example 1, and processed. 97.4% of 6-amino-1-hydroxyhexylidene-1,1-bisphosphonic acid were isolated.

Analysis Mol mass according to pH-titration: 275.7; calc. 277. Paper chromatogram: pure compound Melting point: 208° C.

| Elementary Analysis: | | | | |
|---|---|---|---|---|
| % | P | C | N | H |
| found | 22.6 | 26.0 | 5.18 | 6.45 |
| calc. | 22.38 | 25.99 | 5.05 | 6.14 |

EXAMPLE 4

0.5 mol of 6-aminocaproic acid were reacted with 1 mol phosphorous acid and 1 mol of phosphoryl chloride as described in detail in Example 1, and processed.

Yield: 69.0 gm = 49.8% of 6-amino-1-hydroxyhexylidene-1,1-bisphosphonic acid. Analysis Mol Mass according to pH-titration: 274.2; calc. 277. Paper chromatogram: pure compound Melting point: 209° C.

| Elementary Analysis: | | | | |
|---|---|---|---|---|
| % | P | C | N | H |
| found | 22.3 | 26.0 | 5.16 | 6.47 |
| calc. | 22.38 | 25.99 | 5.05 | 6.14 |

EXAMPLE 5

The sequestering power was determined with the Hampshire test, by adding a calcium salt solution to a sodium carbonate solution containing the sequestrant.

| Phosphonic Acid | Mg CaCO$_3$/gm Acid |
| --- | --- |
| 4-amino-1-hydroxybutylidene-1,1-bis-phosphonic acid | 600 |
| 6-amino-1-hydroxyhexylidene-1,1-bis-phosphonic acid | 400 |

EXAMPLE 6

The results of the sequestering power according to the modified Hampshire test, that is, the dissolution of the freshly precipitated CaCO$_3$, show particularly clearly the good efficacy of the substances as alkaline earth sequestrants.

| Phosphonic Acid | gm-ions Ca/mol Acid |
| --- | --- |
| 4-amino-1-hydroxybutylidene-1,1-bis-phosphonic acid | 1.5 |
| 6-amino-1-hydroxyhexylidene-1,1-bis-phosphonic acid | 2.0 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the preparation of a ω-amino-1-hydroxyalkylidine-1,1-bisphosphonic acid of the formula:

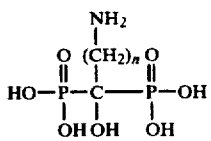

wherein n is an integer from 3 to 5, consisting essentially of the steps of:
(1) reacting an aminocarboxylic acid of the formula:

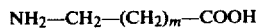

wherein m is an integer from 2 to 4, with a phosphonating reactant selected from the group consisting of:
(a) a mixture of phosphorous acid and PCl$_3$,
(b) a mixture of phosphorous acid and PCl$_5$, and
(c) a mixture of phosphorous acid and POCl$_3$
(2) hydrolyzing the reaction mixture with concentrated hydrochloric acid which does not oxidize aminophosphonic acids, by heating, and
(3) recovering said ω-amino-1-hydroxyalkylidene-1,1-bisphosphonic acid.

2. The process of claim 1 wherein the reaction with said phosphonating reactant is conducted in the presence of an inert organic diluent which does not solublize the reaction product and the diluent is removed prior to said hydrolyzing step.

3. The process of claim 1 or 2 wherein said reaction with a phosphonating reactant is conducted at a temperature of from 80° C. to 130° C.

4. 6-Amino-1-hydroxyhexylidene diphosphonic acid of the summary formula (1):

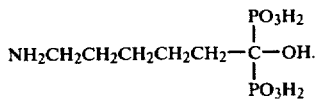

* * * * *